XXX

(12) United States Patent
Stangl et al.

(10) Patent No.: US 11,219,585 B2
(45) Date of Patent: Jan. 11, 2022

(54) PROTECTION AGAINST EXTRINSIC SKIN AGING

(71) Applicant: LA PRAIRIE GROUP AG, Volketswil (CH)

(72) Inventors: Daniel Stangl, Meggen (CH); Bernhard Dudler, Hinwil (CH)

(73) Assignee: LA PRAIRIE GROUP AG, Volketswil (CH)

( * ) Notice: Subject to any disclaimer, the term of this patent is extended or adjusted under 35 U.S.C. 154(b) by 1201 days.

(21) Appl. No.: 15/032,157

(22) PCT Filed: Oct. 30, 2014

(86) PCT No.: PCT/EP2014/002916
§ 371 (c)(1),
(2) Date: Apr. 26, 2016

(87) PCT Pub. No.: WO2015/062727
PCT Pub. Date: May 7, 2015

(65) Prior Publication Data
US 2016/0256379 A1  Sep. 8, 2016

(30) Foreign Application Priority Data

Oct. 31, 2013  (DE) .......................... 102013222168.1

(51) Int. Cl.
| | | |
|---|---|---|
| *A61K 8/64* | (2006.01) | |
| *A61K 9/107* | (2006.01) | |
| *A61K 47/46* | (2006.01) | |
| *A61K 47/10* | (2017.01) | |
| *A61K 38/16* | (2006.01) | |
| *A61K 9/06* | (2006.01) | |
| *A61K 36/11* | (2006.01) | |
| *A61K 36/258* | (2006.01) | |
| *A61K 8/9728* | (2017.01) | |
| *A61K 8/9741* | (2017.01) | |
| *A61K 8/9789* | (2017.01) | |
| *A61K 8/02* | (2006.01) | |
| *A61K 8/06* | (2006.01) | |
| *A61K 8/34* | (2006.01) | |
| *A61K 8/49* | (2006.01) | |
| *A61Q 17/04* | (2006.01) | |
| *A61Q 19/08* | (2006.01) | |
| *A61Q 17/00* | (2006.01) | |
| *A61K 8/36* | (2006.01) | |

(52) U.S. Cl.
CPC ............ *A61K 8/345* (2013.01); *A61K 8/0216* (2013.01); *A61K 8/062* (2013.01); *A61K 8/34* (2013.01); *A61K 8/36* (2013.01); *A61K 8/498* (2013.01); *A61K 8/4973* (2013.01); *A61K 8/64* (2013.01); *A61K 8/9728* (2017.08); *A61K 8/9741* (2017.08); *A61K 8/9789* (2017.08); *A61K 9/06* (2013.01); *A61K 9/107* (2013.01); *A61K 36/11* (2013.01); *A61K 36/258* (2013.01); *A61K 38/164* (2013.01); *A61K 38/168* (2013.01); *A61K 47/10* (2013.01); *A61K 47/46* (2013.01); *A61Q 17/00* (2013.01); *A61Q 17/04* (2013.01); *A61Q 19/08* (2013.01); *A61K 2800/596* (2013.01); *A61K 2800/74* (2013.01)

(58) Field of Classification Search
CPC .... A61K 36/258; A61K 36/11; A61K 38/164; A61K 8/9741; A61K 8/9728
See application file for complete search history.

(56) References Cited

U.S. PATENT DOCUMENTS

| | | |
|---|---|---|
| 5,840,309 A | 11/1998 | Herstein |
| 6,524,626 B2 | 2/2003 | Chen |
| 2002/0012644 A1 | 1/2002 | Chen |
| 2003/0152544 A1 | 8/2003 | Chen |
| 2012/0064182 A1 | 3/2012 | Gohla et al. |
| 2013/0287714 A1 | 10/2013 | Gohla et al. |

FOREIGN PATENT DOCUMENTS

| | | |
|---|---|---|
| FR | 2265401 A1 | 10/1975 |
| FR | 2273551 A1 | 1/1976 |
| FR | 2696932 A1 | 4/1994 |
| WO | 2010086754 A2 | 8/2010 |
| WO | 2012069073 A1 | 5/2012 |

OTHER PUBLICATIONS

Chapter 84: Solutions, Emulsions, Suspensions, and Extractives Nairn, JG. "Solutions, Emulsions, Suspensions, and Extractives" from Remington's Pharmaceutical Science: 17th Ed. Joseph P. Remington. Mack Publishing Co., 1985. pp. 1492, 1513, 1516-1517. (Year: 1985).*
Translation of WO2012069073. (Year: 2012).*
*Saccharomyces.* Retrieved from the internet on: Feb. 28, 2019. Retrieved from: <URL: https://en.wikipedia.org/wiki/Saccharomyces>. 4 pages. (Year: 2019).*
Lactobacillus. Retrieved from the internet on: Feb. 28, 2019. Retrieved from: <https://en.wikipedia.org/wiki/Lactobacillus>. 12 pages. (Year: 2019).*
Vance, J. "Dry Skin" From Beauty to Die For. iUniverse: Nebraska. 3 pages. (Year: 1999).*
"Luxurious travel set", GNPD; MINTEL, Dec. 31, 2007.

* cited by examiner

*Primary Examiner* — Amy L Clark
(74) *Attorney, Agent, or Firm* — Abel Schillinger, LLP

(57) ABSTRACT

The invention is a cosmetic or dermatological preparation and the use thereof, said preparation comprising a combination of a) glycoprotein 1, b) glycoprotein 2, *ginseng* extract and d) *equisetum* extract, to protect the skin against extrinsic skin aging.

22 Claims, 3 Drawing Sheets

PROTECTION AGAINST EXTRINSIC SKIN AGING

BACKGROUND OF THE INVENTION

1. Field of the Invention

The invention is the use of the combination of a) glycoprotein 1, b) glycoprotein 2, c) *ginseng* extract and d) horsetail extract for protecting the skin against extrinsic skin aging.

Preferably, the combination is provided and used in the form of cosmetic or dermatological preparations.

The term "skin aging" is used to refer to the complex biological process of the change in the skin associated with aging. A distinction is made here between intrinsic skin aging, caused by internal physiological and genetic factors, and extrinsic skin aging.

2. Discussion of Background Information

Extrinsic skin aging is attributable to external factors such as e.g. environmental factors such as UV light, chemical reagents, mechanical stress, cigarette smoke, stress or air pollution. Since UV radiation is the main cause of extrinsic skin aging, the term "photoaging" is also used.

The extrinsic factors lead, for example, to wrinkling, skin fatigue, loss of elasticity and dry appearance of the skin.

Intrinsic skin aging, also called chronological skin aging, is caused by internal physiological and genetic factors and reflects degradation processes in the skin. These processes are primarily attributable to a reduced proliferation activity of the skin cells, a reduced synthesis of the matrix proteins and an increase in the expression of matrix-degrading enzymes.

Aged cells exhibit resistance to apoptotic signals, which leads to the accumulation in the tissue of nonproliferating aged cells with altered gene expression pattern.

Skin aging often results in the formation of wrinkles and lines and the loss of elasticity and tone.

Skin aging and wrinkling can be delayed to a decisive extent by corresponding skin protection. In this regard, a large number of options are presented in the prior art, such as, for example, from a healthy lifestyle to topical cosmetic and dermatological preparations.

U.S. Pat. No. 584,030 describes the combination of a) glycoprotein 1, b) glycoprotein 2, c) *ginseng* extract and d) horsetail extract for stimulating the proliferation of fibroblasts and keratinocytes.

It is desirable to provide preparations which are effective against extrinsic skin aging.

SUMMARY OF THE INVENTION

The invention is the use of the combination of
a) glycoprotein 1 obtainable from the purified cytoplasmatic fraction from yeasts (*Saccharomyces*),
b) glycoprotein 2 obtainable from the purified cytoplasmatic fraction from *Lactobacillus*,
c) *ginseng* extract and
d) horsetail extract (*Equisetum Arvense* extract)
for protecting the skin against extrinsic skin aging.

The combination of the constituents a), b), c) and d) is referred to hereinbelow as extract combination and/or as GPVE extract.

The extract comprising a), referred to therein as GP extract, can be produced by biotechnological means from an aqueous cell extract of a purified cytoplasmatic fraction of a natural, selected strain of the yeast *Saccharomyces cerevisiae*. The extract contains glycoproteins and a large number of cellular nutrients and factors.

The extract comprising b), c) and d), referred to as VE extract, and can be obtained by a multistage biotechnological process using *Lactobacillus casei*. *Lactobacillus casei*, which are particularly rich in lytic enzymes, are transferred to a fermentation culture medium where they are able to grow. This medium also comprises protein-rich green microalgae. Under certain fermentation conditions, these lactobacillae can grow exponentially and they produce enzymes which are transferred to the medium. These enzymes attack the cell walls of the algae and open them so that their nutrient-rich cytoplasma is released into the medium.

While the fermentation process progresses, the nutrients in the medium are consumed and if the nutrients become scarce, their growth comes to an end and ultimately the lactobacillae decompose as a result of autolysis. The cell walls open and the contents of the cells, primarily proteins, enzymes, vitamins etc., are released into the medium. At this stage, the process is stopped, the entire medium "harvested", removed from algae remains and filtered. The resulting filtrate constitutes the complete cellular nutrient system (CNS), and is called *Lactobacillus* Ferment.

This ferment b) is supplemented with extracts from horsetail d) and e.g. *ginseng* root c) in order to form the end VE extract.

Glycoprotein 1 is commercially available for example e.g. from DSM, Switzerland, and comprises a purified cytoplasmatic fraction of *Saccharomyces* (*SACCHAROMYCES CEREVISIAE* EXTRACT). It consists of a mixture of amino acids, nucleic acids, nucleotides, carbohydrates, lipids, trace elements, vitamins and phosphatase enzymes. Glycoprotein 2 is commercially available for example e.g. from Sederma, France, and comprises a purified cytoplasmatic fraction from *Lactobacillus*, comprising a mixture of amino acids, nucleic acids, nucleotides, carbohydrates, lipids, trace elements, vitamins and phosphatase enzymes (e.g. *LACTOBACILLUS* FERMENT).

The *ginseng* extract is obtainable for example by extraction with a hydrophilic solvent (in particular water, ethanol, glycol, or any desired mixtures thereof) from the root of *Panax ginseng*. It comprises saponins, sterols, carbohydrates, pectin, vitamins, minerals and lipids (e.g. *PANAX GINSENG* ROOT EXTRACT).

Horsetail extract is obtainable for example by extraction with a hydrophilic solvent (e.g. water, ethanol, glycol, or any desired mixtures thereof) of the entire plant of *Equisetum arvense*. It comprises silicates, flavonoids, saponosides, caffeic acid and ferulic acid (e.g. *EQUISETUM ARVENSE* EXTRACT).

Also in accordance with the invention is a cosmetic or dermatological preparation comprising one or more GPVE extracts and one or more compounds selected from the group glycerol, sodium dehydroacetate, phenoxyethanol, potassium sorbate and/or ethylhexylglycerol, preferably all of the specified compounds.

The GPVE extract and its constituents can be used in any desired concentration in cosmetic or dermatological preparations.

Preferably, the fraction of one of the GPVE extracts, i.e. one or more extract combinations a.) to d.), in the preparation is up to 15% by weight, particularly preferably up to 5% by weight, especially in the range from 0.0001 to 0.5% by weight, based on the total mass of the preparation.

An extract combination or GPVE extract here always comprises all 4 constituents, a.) to d.). However, their particular fraction can be varied depending on markedness.

The fraction of extracts according to the invention is defined as the ratio of the mass of the pure extract, without solvent or extractant, to the total mass of the preparation.

The preparations according to the invention can be present in the known form and types. A known form of the preparations are known as leave-on preparations, such as creams, lotions or body milk. These are often formulated as emulsions, in particular W/O, O/W, O/W/O or W/O/W emulsions. Similarly, the preparations may be dispersions, gels, aqueous or alcoholic solutions, sera, oils, wipe impregnation media, tinctures or ointments. The extracts can advantageously also be applied to the skin in the form of or integrated into wipes, plasters, bandages, patches or pads.

Simply the addition of glycerol, sodium dehydroacetate, phenoxyethanol, potassium sorbate and/or ethylhexylglycerol permits the provision of the combination a.-d. in a cosmetic preparation form.

BRIEF DESCRIPTION OF THE DRAWINGS

In the accompanying drawings.

It is known that mitochondria are responsible for generating energy in human cells. They are located in the cytoplasm and serve as "batteries" for the cells in order to produce, store and distribute energy. The human cell contains on average 1500 mitochondria. Cells with a high metabolic performance (e.g. muscles or the liver) contain more mitochondria. The mitochondria move in the cytoplasm according to the needs of the cell. They are equipped with their own DNA and can therefore reproduce autonomously independently of the cell division. Without the mitochondria, the cell is unable to function and no life is possible.

If these powerhouses of the cells do not work correctly, this can increase the rate of aging processes in the skin. Defects in the mitochondria, in particular also in the mitochondrial DNA, can therefore increase the rate of aging.

Protection of the mitochondrial functionality against extrinsic disturbance factors, e.g. against UV radiation and oxidative stress, and/or ensuring the integrity of the mitochondria is therefore effective protection against skin aging and, according to the invention, therefore belongs to one of the essential protective applications against extrinsic skin aging.

An investigation shows the protection of mitochondrial DNA under UV irradiation by the combination according to the invention.

On the mitochondrial DNA (mtDNA) are located some, but not all, of the genes for the enzymes of the respiratory chain, as well as genes which are responsible for the structure and reproduction of the mitochondria. Damage can occur very easily at the mtDNA, but this is however unprotected in the mitochondria and is exposed there to the free radicals which may form during the production of energy. Damage at the mtDNA can therefore lead to a serious impairment of the cellular energy production.

One of the most common forms of damage to the mtDNA is known as "common deletion", which is detected in the subsequent assay.

HaCaT cells are cells of a specific human keratinocyte cell line. Cultivated keratinocytes (HaCaT) are incubated with various compounds for 48 h and then stressed with UVB radiation (1.5 mJ/cm$^2$ for 1 h). The cells are then collected and lysed for DNA extraction. With the aid of the intensity of the common deletion band, expressed as a ratio of the common deletion compared to the standard, it is possible to determine the protection against damage by UV light.

Figure 1:
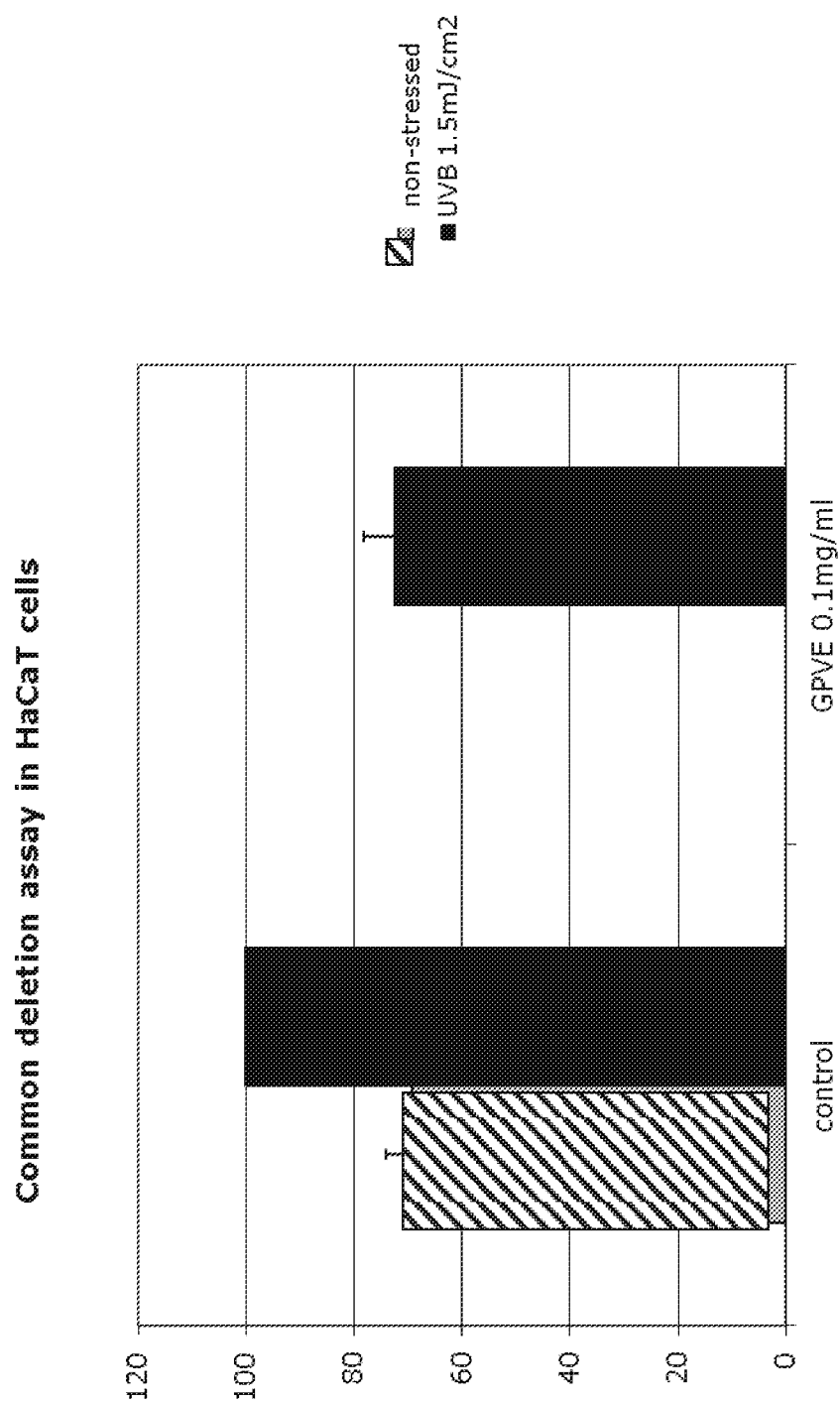
FIG. 1 is a bar diagram relating to the common deletion assay in HaCaT cells.

FIG. 1 shows that the combination according to the invention, particularly in a cosmetic preparation with the optional constituents, reduces the UV-induced damage to the mitochondrial DNA in keratinocytes (HaCaT cells) by approx. 90% relative to the control.

Investigations were carried out for 0.1 mg/ml of GPVE extracts according to the invention in a preparation comprising glycerol, sodium dehydroacetate, phenoxyethanol, potassium sorbate and ethylhexylglycerol.

Significant protection is observed, as FIG. 1 shows, with a 92% reduction in the UVB-induced DNA damage (common deletion test) compared to the control.

DNA damage leads to an impairment of cellular functions and ultimately to skin aging. UV radiation is the essential factor in premature skin aging and therefore an extrinsic factor against which the use according to the invention protects.

Epidermal and dermal stem cells or their descendants are significantly involved in the routine maintenance and renewal of the corresponding skin layer. Protection of these cells against external stresses such as UV radiation or free radicals thus contributes significantly to the maintenance of a youthful, healthy and beautiful skin.

The preparation according to the invention with GPVE extract, for example in a fraction of 0.125% by weight, based on the total mass of the preparation, protects the proliferation potential of epidermal stem cells under oxidative stress. This is measured by the ability of the cells to form colonies in vitro (colony-forming efficiency=CFE). The following experiments were carried out in this regard.

Primary human epidermal keratinocyte precursor cells are sown in the presence of the preparation with GPVE extract in CnT-07 culture media and left to grow for 48 hours. The test patterns are then exposed to different concentrations of hydrogen peroxide. Afterwards, the cells are sown for the CFE assays. For the CFE evaluation, the cells are sown at a low density and cultivated for 10 days. The cultures are then fixed, stained and the colonies are counted. The CFE evaluations are carried out three times. Untreated cells are used as the control.

Figure 2:
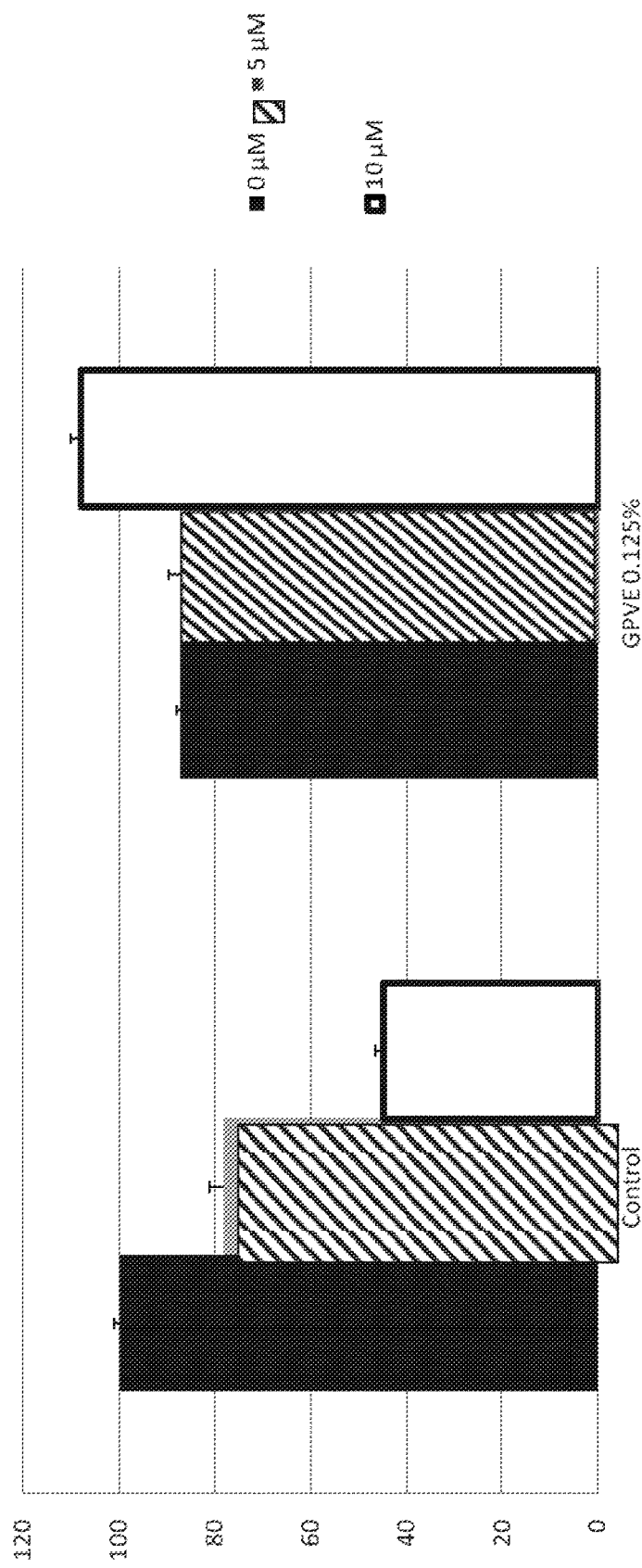
FIG. 2 is a bar diagram comparing the relative efficiency of colony formation following peroxide treatment in the presence and absence of an extract of the invention.

As the results in FIG. 2 show, the preparation according to the invention comprising GPVE extracts significantly protects the proliferation potential of the epidermal stem cells against oxidative stress by hydrogen peroxide. For example, the number of colonies formed in the presence of the extract increases by more than double compared to the untreated control with 10 μM hydrogen peroxide.

The GPVE extract preferred according to the invention or the preparations comprising it protect the proliferation potential of epidermal stem cells under UV and oxidative stress, measured by the ability of the cells to form colonies in vitro (colony-forming efficiency=CFE). The following experiments were carried out in this regard:

UV Irradiation:

With two selected concentrations, the primary epidermal keratinocyte precursor cells are sown in the presence of each compound in CnT-07 culture medium and left to grow for 48 hours. Each test is then subjected to an irradiation with a UVA and UVB light source either 1200 mJ or 1800 mi. A test with non-irradiated sample is also carried out. After the exposure, the cells are sown for the CFE assay. For the CFE evaluation, the cells are sown with a low density and cultivated for 10 days. The cultures are then fixed and stained and the colonies are counted. The CFE evaluations are carried out three times. Untreated cells are used as the control. The GPVE extract protects dermal stem cells against the negative effects of UV radiation on their proliferation ability. Consequently, the surprising use option of the GPVE extracts for protecting the skin against extrinsic skin aging also becomes evident.

The following experiment was carried out in this regard: dermal precursor cells (isolated from dermal papilla) are cultivated in monolayers in the presence or absence of the extracts for a period of 2 days, then irradiated with a UVA and UVB light source with a dose of 1200 mJ or 1800 mJ.

A sphere formation is evaluated after approx. 5 days of the culture.

Figure 3:
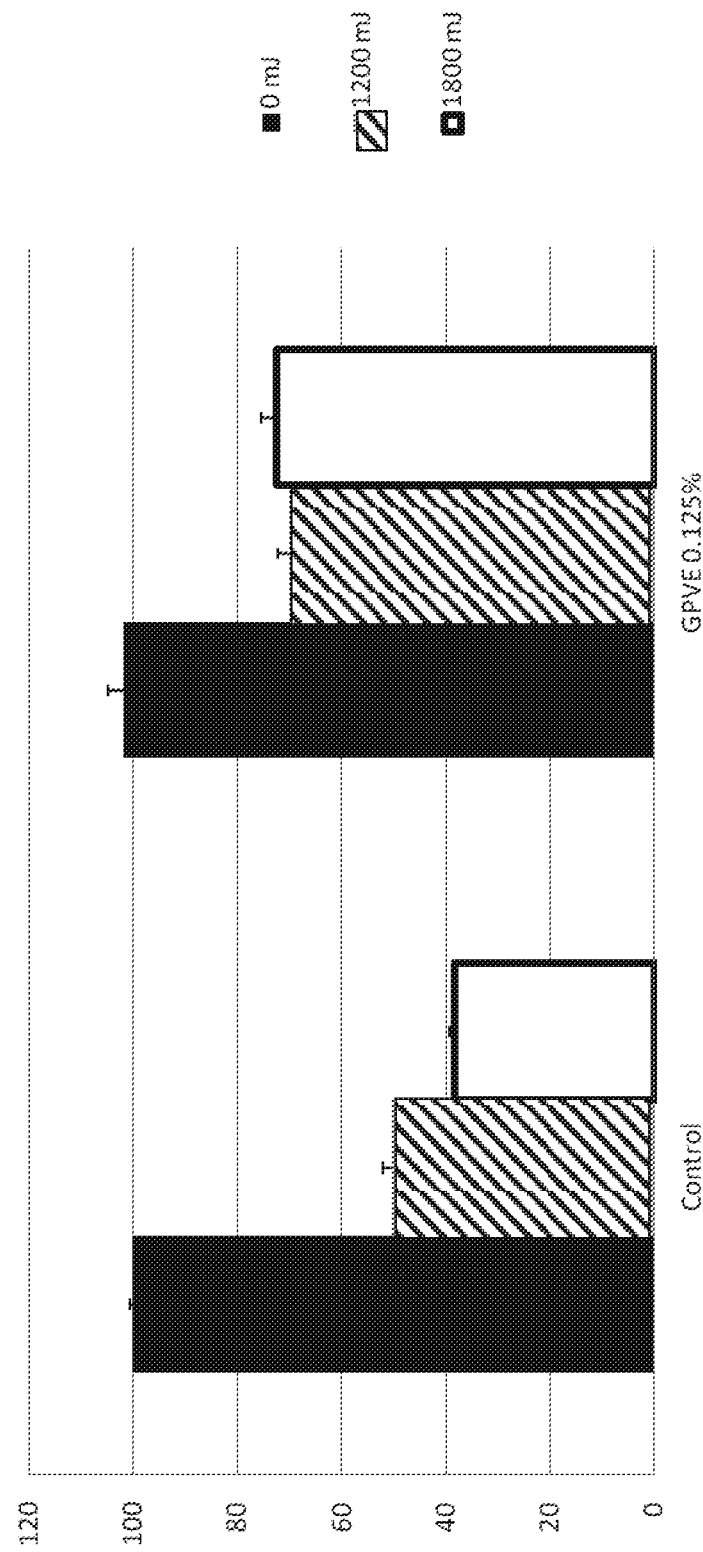
FIG. 3 is a bar diagram comparing the relative efficiency of the formation of spheres following UV irradiation with and without extract of the invention.

The proliferation ability of the dermal stem cells is ascertained by reference to their ability to form spherical colonies (spheres). If the number of spheres formed in the control (without extracts) drops by 50% or 62% under UV irradiation (1200 mJ or 1800 mJ), then the number of spheres in the presence of GPVE increases by 40% or 92% respectively (FIG. 3).

The preparations according to the invention with GPVE extracts have a stimulating effect on the synthesis of important skin lipids in the epidermis. These lipids, in particular ceramides, are essential for the construction of an intact skin barrier. The following experiment was carried out in this regard.

Human epidermal keratinocytes were sown in a culture medium, cultivated for 24 hours, after incubation for a further 7 days in the medium washed in the presence of radioactively labeled acetate, with and without GPVE extract and with calcium chloride/vitamin C as positive control, and lysed. The cell extracts thus obtained were analyzed by means of thin layer chromatography and the individual spots were quantified via their radioactivity.

Result:

The GPVE extract significantly stimulates the synthesis of the most important classes of skin lipids as follows:

| Lipid class | % GPVE | Stimulation (% control) |
| --- | --- | --- |
| Sphingomyelins | 0.0007 | 121 |
| Phospholipids | 0.0062 | 137 |
| Cholesterol sulfate | 0.002 | 126 |
| Polar ceramides and cerebrosides | 0.002 | 131 |
| Low-polarity ceramides and cerebrosides | 0.0007 | 160 |

Unexpectedly, the extract stimulates the synthesis of sphingomyelin, phospholipids, cholesterol sulfate, ceramides and cerebrosides in human keratinocytes. The fraction of GPVE extracts in the application preparation here is only 0.0007 to 0.002% by weight.

The preparations according to the invention and in particular the GPVE extract can therefore preferably be used for the following protection and/or stimulation:
1. Protection of the epidermal stem cells against oxidative stress
2. Protection of the dermal stem cells against UV light
3. Stimulation of the lipid synthesis All three effects were unexpected.

The experiments presented demonstrate the application possibility of the extract combination (GPVE) of
a) glycoprotein 1 obtainable from the purified cytoplasmatic fraction from yeasts (*Saccharomyces*),
b) glycoprotein 2 obtainable from the purified cytoplasmatic fraction from *Lactobacillus*,
c) *ginseng* extract and
d) horsetail extract (*Equisetum Arvense* extract)
and optionally additionally glycerol, sodium dehydroacetate, phenoxyethanol, potassium sorbate and ethylhexylglycerol, advantageously in the form of cosmetic or dermatological preparations, as protection against skin damage which can arise as a result of extrinsic factors.

The cosmetic or dermatological preparations according to the invention can also comprise auxiliaries and further active ingredients as are customarily used in such preparations, e.g. substances for preventing foaming, dyes and colored pigments, thickeners, moisturizing and/or humectant substances, fats, oils, waxes or other customary constituents of a cosmetic or dermatological formulation, such as alcohols, polyols, polymers, foam stabilizers, electrolytes, organic solvents or silicone derivatives, provided the addition does not adversely affect the required properties with regard to the protective function and stimulation.

The preparation according to the invention comprising one or more GPVE extracts preferably comprises one or more compounds selected from the group glycerol, sodium dehydroacetate, phenoxyethanol, potassium sorbate and/or ethylhexylglycerol, preferably all of the specified compounds. Surprisingly, these preparations have proven to be particularly stable and skin-compatible, such that the described protective functions and stimulations can also take place in the daily application.

Moreover, it was found that these constituents help to further increase the protective function of the GPVE extracts.

Consequently, a cosmetic or dermatological preparation comprising one or more GPVE extracts and one or more compounds selected from the group glycerol, sodium dehydroacetate, phenoxyethanol, potassium sorbate and/or ethylhexylglycerol, preferably all of the specified compounds, is in accordance with the invention.

One or more GPVE extracts can be used for reducing or avoiding skin damage by extrinsic factors.

One or more GPVE extracts can be used for producing pharmaceutical, in particular dermatological, preparations and serve for the reduction or avoidance of skin damage due to extrinsic factors.

The extracts according to the invention are preferably present in topical preparations.

In particular, the topical preparation is a cosmetic preparation.

In the event of limitations to substances specified as preferred, be they the extracts, lipids or active ingredients or further constituents specified as being preferred, then their preferred fraction ranges also refer to the individual constituents then selected. The others, the constituents excluded by the limitation, then no longer count towards the listed fraction ranges.

Examples below illustrate the preparations according to the invention.

EXAMPLE 1

O/W Emulsion with SPF

This preparation can advantageously also comprise the following components: peptides, plant extracts, extracts of plant stem cells, biopolymers, vitamins, antioxidants.

| INCI name | % by weight |
| --- | --- |
| WATER (AQUA) | 53.7277 |
| ETHYLHEXYL METHOXYCINNAMATE | 7.5000 |
| ETHYLHEXYL SALICYLATE | 5.0000 |
| C12-15 ALKYL ETHYLHEXANOATE | 5.0000 |
| GLYCERIN | 3.5238 |
| DIMETHICONE/VINYL DIMETHICONE CROSSPOLYMER | 3.2125 |
| BUTYL METHOXYDIBENZOYLMETHANE | 3.0000 |
| POLYGLYCERYL-3 METHYLGLUCOSE DISTEARATE | 2.5500 |
| OCTOCRYLENE | 2.5000 |
| *HELIANTHUS ANNUUS* (SUNFLOWER) SEED OIL UNSAPONIFIABLES | 2.0000 |
| BEHENYL ALCOHOL | 1.5000 |
| STEARETH-21 | 1.5000 |
| BUTYLENE GLYCOL | 1.4100 |
| CAPRYLIC/CAPRIC TRIGLYCERIDE | 0.9650 |
| HYDROGENATED LECITHIN | 0.5040 |
| TOCOPHERYL ACETATE | 0.5000 |
| CETYL DIMETHICONE | 0.5000 |
| CAPRYLYL GLYCOL | 0.4200 |
| STEARETH-2 | 0.4000 |
| PEG-100 STEARATE | 0.3750 |
| GLYCERYL STEARATE | 0.3750 |
| POTATO STARCH MODIFIED | 0.3000 |
| POLYACRYLAMIDE | 0.2625 |
| CARNOSINE | 0.2500 |
| PANTHENOL | 0.2500 |
| DISODIUM EDTA | 0.2080 |
| SODIUM PCA | 0.2000 |
| CARBOMER | 0.2000 |
| UREA | 0.2000 |
| C13-14 ISOPARAFFIN | 0.1275 |
| ALCOHOL | 0.1105 |
| ALLANTOIN | 0.1000 |
| LAURETH-7 | 0.0600 |
| SYNTHETIC WAX | 0.0460 |
| SILICA | 0.0375 |
| SODIUM HYDROXIDE | 0.0330 |
| POLYQUATERNIUM-51 | 0.0252 |
| SODIUM HYALURONATE | 0.0180 |
| TRIACETIN | 0.0080 |
| *GLYCINE SOJA* (SOYBEAN) OIL | 0.0080 |
| HYDROXYETHYL BEHENAMIDOPROPYL DIMONIUM CHLORIDE | 0.0070 |
| POLYSORBATE 80 | 0.0060 |
| *LACTOBACILLUS* FERMENT | 0.0052 |
| DEXTRAN | 0.0018 |
| *PANAX GINSENG* ROOT EXTRACT | 0.0018 |
| *SACCHAROMYCES CEREVISIAE* EXTRACT | 0.0018 |
| POLYQUATERNIUM-67 | 0.0010 |
| *EQUISETUM ARVENSE* EXTRACT | 0.0009 |
| ETHYLHEXYLGLYCERIN | 0.0005 |
| SODIUM OLEATE | 0.0004 |
| GLYCOPROTEINS | 0.0003 |
| FRAGRANCE (PARFUM) | 0.4333 |
| PHENOXYETHANOL | 0.5621 |
| SORBIC ACID | 0.0625 |
| CHLORPHENESIN | 0.0030 |
| METHYLPARABEN | 0.0014 |
| BENZOIC ACID | 0.0012 |
| SODIUM DEHYDROACETATE | 0.0011 |
| POTASSIUM SORBATE | 0.0007 |
| YELLOW 5 | 0.0005 |
| RED 4 | 0.0003 |
| | 100.0000 |

EXAMPLE 2

Serum

This preparation can advantageously also comprise the following components: peptides, plant extracts, extracts of plant stem cells, biopolymers, vitamins, antioxidants.

| INCI name | % by weight |
| --- | --- |
| WATER (AQUA) | 74.6950 |
| PROPYLENE GLYCOL | 5.6991 |
| SD ALCOHOL 40-B (ALCOHOL DENAT.) | 5.3001 |
| BIS-PEG-18 METHYL ETHER DIMETHYL SILANE | 4.3000 |
| GLYCERIN | 3.1381 |
| PENTYLENE GLYCOL | 1.6500 |
| SEA WATER (MARIS AQUA) | 0.9800 |
| ETHYLHEXYL PALMITATE | 0.9530 |
| PANTHENOL | 0.6000 |
| ACRYLATES/C10-30 ALKYL ACRYLATE CROSSPOLYMER | 0.3000 |
| XANTHAN GUM | 0.2500 |
| HDI/TRIMETHYLOL HEXYLLACTONE CROSSPOLYMER | 0.1960 |
| ISOMALT | 0.1850 |
| BUTYLENE GLYCOL | 0.1600 |
| DISODIUM EDTA | 0.1040 |
| ETHYLHEXYL METHOXYCINNAMATE | 0.1000 |
| HYDROXYETHYLCELLULOSE | 0.1000 |
| BUTYL METHOXYDIBENZOYLMETHANE | 0.0960 |
| PPG-26-BUTETH-26 | 0.0920 |
| SODIUM HYDROXIDE | 0.0783 |
| ETHYLHEXYL SALICYLATE | 0.0600 |
| SODIUM HYALURONATE | 0.0520 |
| PEG-40 HYDROGENATED CASTOR OIL | 0.0520 |
| ETHYLHEXYLGLYCERIN | 0.0500 |
| DISODIUM ADENOSINE TRIPHOSPHATE | 0.0300 |
| SILICA DIMETHYL SILYLATE | 0.0250 |
| LECITHIN | 0.0210 |
| ALCOHOL | 0.0200 |
| CAPRYLYL GLYCOL | 0.0060 |
| ALGIN | 0.0055 |
| SILICA | 0.0040 |
| *GLYCINE SOJA* (SOYBEAN) OIL | 0.0020 |
| HYDROGENATED LECITHIN | 0.0020 |
| SODIUM CHLORIDE | 0.0018 |
| *LACTOBACILLUS* FERMENT | 0.0017 |
| SODIUM PHOSPHATE | 0.0014 |
| HEXYLENE GLYCOL | 0.0010 |
| EDTA | 0.0010 |
| POLYSORBATE 80 | 0.0010 |
| *SACCHAROMYCES CEREVISIAE* EXTRACT | 0.0006 |
| *PANAX GINSENG* ROOT EXTRACT | 0.0006 |
| *EQUISETUM ARVENSE* EXTRACT | 0.0003 |
| SODIUM OLEATE | 0.0002 |
| GLYCOPROTEINS | 0.0001 |
| FRAGRANCE (PARFUM) | 0.2030 |
| PHENOXYETHANOL | 0.4774 |
| POTASSIUM SORBATE | 0.0019 |
| SODIUM BENZOATE | 0.0007 |
| SODIUM DEHYDROACETATE | 0.0004 |
| EXT. VIOLET 2 | 0.0007 |
| BLUE 1 | 0.0001 |
| | 100.0000 |

What is claimed is:

1. A topical cosmetic or dermatological preparation, wherein the preparation protects skin, comprising a combination of:

(a) glycoprotein 1, obtained from a purified cytoplasmatic fraction from *Saccharomyces cerevisiae;*

(b) glycoprotein 2, obtained from a purified cytoplasmatic fraction from *Lactobacillus;*

(c) *ginseng* extract; and (d) horsetail extract (*Equisetum Arvense* extract), and further comprises one or more compounds selected from glycerol, sodium dehydroacetate, phenoxyethanol, potassium sorbate, and ethylhexylglycerol.

2. The preparation of claim 1, wherein sodium dehydroacetate is present.

3. The preparation of claim 1, wherein potassium sorbate is present.

4. The preparation of claim 1, wherein ethylhexylglycerol is present.

5. The preparation of claim 1, wherein phenoxyethanol is present.

6. The preparation of claim 1, wherein at least two of glycerol, sodium dehydroacetate, phenoxyethanol, potassium sorbate, ethylhexylglycerol are present.

7. The preparation of claim 1, wherein at least three of glycerol, sodium dehydroacetate, phenoxyethanol, potassium sorbate, ethylhexylglycerol are present.

8. The preparation of claim 1, wherein glycerol, sodium dehydroacetate, phenoxyethanol, potassium sorbate, and ethylhexylglycerol are present.

9. The preparation of claim 1, wherein (a) to (d) are present in a concentration of up to 5% by weight, based on the total weight of the preparation.

10. The preparation of claim 9, wherein (a) to (d) are present in a concentration of at least 0.0001% by weight.

11. The preparation of claim 10, wherein (a) to (d) are present in a concentration of up to 0.5% by weight.

12. The preparation of claim 1, wherein the preparation is in the from of an emulsion.

13. The preparation of claim 1, wherein the preparation is in the form of a cream.

14. The preparation of claim 1, wherein glycoprotein 2 is obtained by using *Lactobacillus casei*.

15. The preparation of claim 1, wherein the preparation further comprises at least one UV filter.

16. The preparation of claim 1, wherein the preparation is effective in protecting epidermal stem cells against oxidative stress.

17. The preparation of claim 1, wherein the preparation is effective in protecting dermal stem cells against UV light.

18. The preparation of claim 1, wherein the preparation is effective in stimulating lipid synthesis in human keratinocytes.

19. The preparation of claim 1, wherein the preparation is effective in protecting mitochondrial DNA under UV irradiation.

20. The preparation of claim 1, wherein the preparation is effective in reducing or preventing skin damage by extrinsic factors.

21. The preparation of claim 1, wherein the preparation is in the form of a lotion.

22. The preparation of claim 1, wherein the preparation is in the form of a body milk.

* * * * *